United States Patent [19]

Lau et al.

[11] Patent Number: 4,922,019
[45] Date of Patent: May 1, 1990

[54] DERIVATIVES OF 2,2-BIS-(3-AMINOPHENYL)HEXAFLUORO-PROPANE AND PROCESS FOR THE PREPARATION OF 2,2-BIS-(3,4-DIAMINOPHENYL)HEXA-FLUOROPROPANE

[75] Inventors: Jürgen Lau; Günter Siegemund, both of Hofheim am Taunus, Fed. Rep. of Germany

[73] Assignee: Hoechst Aktiengesellschaft, Frankfurt am Main, Fed. Rep. of Germany

[21] Appl. No.: 212,953

[22] Filed: Jun. 29, 1988

[30] Foreign Application Priority Data

Jul. 2, 1987 [DE] Fed. Rep. of Germany ....... 3721839

[51] Int. Cl.$^5$ .............................................. C07C 87/50
[52] U.S. Cl. .................................... 564/332; 564/330
[58] Field of Search ................................ 564/330, 332

[56] References Cited

U.S. PATENT DOCUMENTS 3,310,573 3/1967 Coe ..................................... 564/332
4,370,501 1/1983 Lau ..................................... 564/330

OTHER PUBLICATIONS

Chemical Abstracts 105(19): 172030.
Lau, K.S.Y. et al., J. Polymer Sci., Polymer Chem, Ed., 20, 2381-93 (1982).

Primary Examiner—Shep K. Rose
Assistant Examiner—Raymond J. Henley, III

[57] ABSTRACT

The invention relates to compounds of the formula

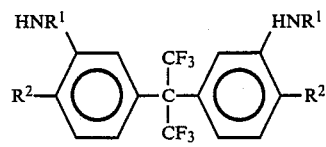

wherein $R^1$ is hydrogen or an acyl group in which a non-aromatic hydrocarbon group of 1 to 6 carbon atoms is attached to the CO-group and $R^2$ is H or $NO_2$, if $R^1$ is an acyl group, or is $NO_2$, if $R^1$ is hydrogen.

The invention further relates to a process for the production of 2,2-bis-(3,4-diaminophenyl)-hexafluoropropane of the formula

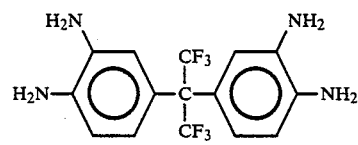

which comprises
(a) acylating 2,2-bis-(3-aminophenyl)-hexafluoropropane, under conditions conventional for acylations, to yield a 2,2-bis-(3-acylamidophenyl)-hexafluoropropane, the acyl group of which is free from aromatic groups,
(b) nitrating the 2,2-bis-(3-acylamidophenly)-hexafluoropropane, under conditions conventional for nitrations, to yield 2,2-bis-(3-acylamido-4-nitrophenyl)-hexafluoropropane,
(c) deacylating the 2,2-bis-(3-acylamido-4-nitrophenyl)-hexafluoropropane, under conditions conventional for deacylations, to yield 2,2-bis-(3-amino-4-nitrophenyl)-hexafluoropropane,
(d) reducing this compound, under conditions conventional for the reduction of nitro compounds, to yield 2,2-bis-(3,4-diaminophenyl)-hexafluoropropane, and
(e) isolating this compound or subjecting it to a purification by converting it into a solution of one of its salts, adsorbing contaminations at an adsorption agent and recipitating the 2,2-bis-(3,4-diaminophenyl)-hexafluoropropane by addition of a base.

16 Claims, No Drawings

DERIVATIVES OF 2,2-BIS-(3-AMINOPHENYL)HEXAFLUOROPROPANE AND PROCESS FOR THE PREPARATION OF 2,2-BIS-(3,4-DIAMINOPHENYL)HEXAFLUOROPROPANE

DESCRIPTION

The invention relates to new derivatives of 2,2-bis-(3-aminophenyl)hexafluoropropane and a new process for the preparation of 2,2-bis-(3,4-diaminophenyl)hexafluoropropane, hereinafter referred to as "the tertamine", a fluorine-containing monomer for polybenzimidazoles.

It has been disclosed in U.S. Pat. No. 3,310,573 to react toluene with hexafluoroacetone in the presence of hydrofluoric acid to give 2,2-bis-(4-methylphenyl)hexafluoropropane (2). This is oxidized to the dicarboxylic acid (3) using chromium(III) oxide, which is subsequently converted into the 2,2-bis-(4-aminophenyl)hexafluoropropane (4) by a Schmidt reaction using sodium azide/sulfuric acid. In the next reaction steps, this compound is acetylated using acetic anhydride and then nitrated in the 3-position using 70% strength nitric acid in concentrated sulfuric acid. The elimination of the acetyl group then takes place, for which the nitrated substance is dissolved in concentrated sulfuric acid and water added until the 2,2-bis-(3-nitro-4-aminophenyl)-hexafluoropropane (5) precipitates from the solution.

The further reaction, i.e. the reduction of the 2,2-bis(3-nitro-4-aminophenyl)hexafluoropropane to the tetramine and the physical properties of the tetramine are neither described in the said U.S. Pat. No. 3,310,573 nor otherwise. Furthermore, the remarks made for the individual steps in the U.S. patent only permit a calculation of the yield for the nitration.

For the possible use of the tetramine as a monomer building block for polymers it is now important that this compound, which is extremely oxidation-sensitive in solution, is accessible easily and in pure form.

The intermediate 2,2-bis-(4-aminophenyl)hexafluoropropane prepared in the 3rd step of the abovementioned process can also be prepared from 2,2-bis-(4-hydroxyphenyl)-hexafluoropropane in a 3-step process according to a new literature source (U.S. Pat. No. 4,370,501 (1983)), in which this is first reacted with a 4-chloroquinazoline derivative of the formula

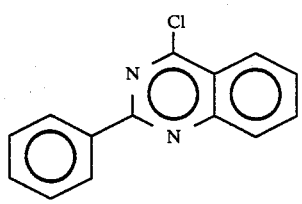

in the presence of potassium hydroxide and dimethyl sulfoxide using a crown ether (18-crown-6) as a catalyst with hydrogen chloride elimination and potassium chloride formation. The diether formed is then rearranged in a second step in an inert atmosphere at about 320° C. to the corresponding bis-quinazoline derivative which is cleaved in a third step to 2,2-bis-(4-aminophenyl)hexafluoropropane by treatment with aqueous potassium hydroxide solution and ethylene glycol.

According to the exemplary embodiments of U.S. Pat. No. 4,370,501, the yields in the 1st step are 65.5%, in the 2nd step 83.5% and in the 3rd step 30.2% of theory.

With respect to 2,2-bis-(4-hydroxyphenyl)hexafluoropropane, the yields in this process for the preparation of anilines and dianilines (see U.S. Pat. No. 4,370,501, column 4), already described as worthwhile and having "high yields", are only 16.5%.

On the other hand, a process is described in the literature (K. S. Y. Lau et al., Journal of Polymer Science, Polymer Chemistry Edition, 20. 2381-2393 (1982)) which facilitates the preparation of an isomeric diamine to 2,2-bis-(4-aminophenyl) hexafluoropropane from, 2,2-bis-(3-aminophenyl)hexafluoropropane, in very high yields. For this, the process also starts out from 2,2-bis-(4-hydroxyphenyl)hexafluoropropane, the hydroxyl groups of which are converted into $F_3C-SO_3$ groups by reaction with trifluoromethanesulfonic anhydride. Trifluoromethanesulfonic acid is eliminated from this compound in a second step by catalytic hydrogenation with a palladium/charcoal catalyst which is suspended in triethylamine and 2,2-bisphenylhexafluoropropane is thus obtained. This compound is nitrated using nitric acid in concentrated sulfuric acid to give 2,2-bis-(3-nitrophenyl)hexafluoropropane in a third step which is then hydrogenated on a palladium/charcoal catalyst to give 2,2-bis-(3-aminophenyl)hexafluoropropane in a fourth step.

According to the embodiment examples, the yields for the individual steps are 96.5% in the 1st step, 87.6% in the 2nd step, 90.0% in the 3rd step and 92.0% of theory in the 4th step.

The starting compound for both the latter processes—2,2-bis-(4-hydroxyphenyl)hexafluoropropane (bisphenol AF)——is a common chemical and can be obtained, for example, by reaction of hexafluoroacetone with phenol in liquid hydrogen fluoride.

A comparison of both the latter processes makes it clear that the 2,2-bis-(3-acetamidophenyl) hexafluoropropane can be prepared with the same starting material in substantially higher yield—70% compared to 16.5%—than the 2,2-bis-(4-aminophenyl)-hexafluoropropane in spite of an additional reaction step.

In endeavoring to make available a simpler and more economical process for the preparation of 2,2-bis-(3,4-diaminophenyl)hexafluoropropane which can be carried out with advantage on the industrial scale, it has now been found that this can also be prepared starting out from 2,2-bis-(3-aminophenyl)hexafluoropropane.

The invention therefore relates to a process for the preparation of 2,2-bis-(3,4-diaminophenyl)hexafluoropropane which comprises (a) converting 2,2-bis-(3-aminophenyl)hexafluoropropane into an acylated compound whose acyl radical is free from aromatic radicals, in particular 2,2-bis-(3-acetamidophenyl)hexafluoropropane (7), under customary acylation conditions, in particular by reaction with acetic anhydride, (b) nitrating this under customary nitration conditions, in particular with nitric acid, to give 2,2-bis-(3-acylamido-4-nitrophenyl)hexafluoropropane, in particular to give 2,2-bis-(3-acetamido-4-nitrophenyl)-hexafluoropropane (8), (c) deacylating the product obtained under the customary conditions for deacylation, for example in the alkaline or acidic range, to give 2,2-bis-(3-amino-4-nitrophenyl)hexafluoropropane (9) and (d) reducing this under the customary conditions for the reduction of nitro compounds to give 2,2-bis-(3,4-diaminophenyl)hexafluoropropane (1).

This tetramine is isolated or—preferably with exclusion of oxygen—converted in solution to one of its salts, preferably a hydrohalide, in particular the hydrochloride; impurities are removed from this by means of an adsorbent, preferably activated charcoal, and the tetramine is precipitated using a base, such as alkali metal hydroxides, alkaline earth metal hydroxides or alkali metal carbonates, preferably aqueous ammonia solution, with the exclusion of oxygen. In this manner, the tetramine can be obtained as a highly pure solid.

If step (c) is carried out using approximately 1-molar methanolic aqueous sodium hydroxide solution and step (d) is carried out on a palladium/charcoal catalyst, then the yields in step (a) are up to 99%,
in step (b) are up to 88%,
in step (c) are up to 87% and
in step (d) are up to 89% of theory.

The purification of the tetramine via the hydrochloride is already allowed for in the yield data for step (d). A white solid is thus obtained which possesses a purity of more than 99.9% according to gas chromatography. The high purity of the solid tetramine is particularly important for its use as a monomer component for the preparation of polybenzimidazoles.

The purification of the tetramine, which is brown-yellow after the reduction, expediently takes place under inert gas (for example nitrogen) via one of its salts, since the tetramine is very sensitive to oxidation in dissolved form.

The process according to the invention is based, however, in its individual process steps on known reactions or reactions which are analogous to known processes, but leads to new intermediates in process steps (a), (b) and (c) which are obtained in high yields. It therefore represents in its entirety a considerable advance, just like the new intermediates, which are likewise the subject of the invention, and the purification of the 2,2-bis-(3,4-diaminophenyl)hexafluoropropane via one of its salts, and opens an advantageous route to the preparation of this compound.

In principle, suitable acylating agents are all customary substances, for example acid halides or acid anhydrides, the reaction in general being performed at temperatures of 0°-50° C., preferably at 5°-20° C. A hydrocarbon radical having 1 to 6 carbon atoms is preferably bonded to the CO group in the acyl radicals $R^1$, i.e. for example alkyl, such as methyl, ethyl and the various propyl, butyl, pentyl and hexyl radicals, the cyclopentyl radical—optionally substituted by methyl—and the cyclohexyl radical.

The customary nitrating acid mixtures, for example nitric acid/sulfuric acid, nitric acid/glacial acetic acid, nitric acid/acetic anhydride or nitric acid/water mixtures can be used for the nitration of the acylated compound. An 85 to 95% by weight nitric acid is particularly suitable for the nitration, the acylated compound expediently being introduced into the nitric acid, preferably at 0°-40° C.

The removal of the acyl groups can be carried out according to the customary deacylation methods. Solutions in water and/or with water-miscible solvents, in particular alcohols which contain 5-50% by weight of a base, for example alkali metal hydroxide or ammonium bases, are particularly suitable in the alkaline medium.

The deacylation in general takes place at temperatures from 0°-100° C. Suitable alcohols are primarily methanol and ethanol.

The reduction of the nitro groups can be carried out, for example, by the customary catalytic methods using hydrogenation catalysts of a transition metal, in particular of group VIII of the periodic table according to Meyer-Mendeleev, or by stoichiometric methods (for example using tin(II) chloride/glacial acetic acid). Platinum metals, copper, iron, cobalt, nickel, metal oxides or mixed metal catalysts, preferably without or with the use of overpressure, in customary diluents such as alcohols, aromatic hydrocarbons (for example toluene), esters or similar organic solvents at temperatures from, for example, 10°-80° C. can be employed for the catalytic reductions.

For the purpose of purification, the tetramine (1) can be converted at, for example, 10°-100° C. in water into one of its water-soluble salts (for example halide, hydrogen sulfate), which is inert towards amino groups under the conditions used.

The preferred new intermediates have the formula II

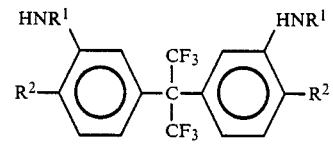

wherein $R^1$ has the abovementioned meaning and $R^2$ represents hydrogen or $NO_2$ or wherein $R^1$ is hydrogen and $R^2$ is $NO_2$. Of the compounds in which $R^1$ represents acyl, those are particularly preferred in which $R^1$ is acetyl. In other words, 2,2-bis-(3-acetamidophenyl)-hexafluoropropane and 2,2-bis-(3-acetamido-4-nitrophenyl)hexafluoropropane are preferred in addition to 2,2-bis-(3-amino-4-nitrophenyl)hexafluoropropane.

EXAMPLES (1) Preparation of 2,2-Bis-(3-acetamidophenyl)hexafluoropropane (7)

66.8 g (0.2 mol) of 2,2-bis-(3-aminophenyl)hexafluoropropane are dissolved in 250 ml of glacial acetic acid and 130 ml of ice water are added. 48.1 g (1.3 mol) of acetic anhydride are added at 5° C. and the mixture is stirred for 30 minutes. The deposited precipitate is filtered off with suction, washed intensively with 500 ml of water and dried at 80° C. Yield 83 g (0.198 mol); white solid; m.p. 309°-311° C.

Analysis values in %:
$C_{19}H_{16}F_6N_2O_2$ calc.: C 54.55, H 3.86, N 6.70, F 27.25, O 8.90.

25 (418.34) found: C 54.1, H 3.8, N 6.5, F 26.7, O 9.2.

$^1$H-NMR ($d^6$-DMSO)δ(ppm): 10.1 s 2 NH, 7.9 - 6.95 m 8 H, 2.05 s 2 $CH_3$.

$^{19}$F-NMR ($d^6$-DMSO(δ(ppm): −62.4 s $CF_3$.

IR (KBr) γ: 3300 $cm^{-1}$ NH, 1670 $cm^{-1}$ C=O 1260-1140 $cm^{-1}$ $CF_3$.

(2) Preparation of 2,2-Bis-(3-acetamido-4-nitrophenyl)hexafluoropropane (8)

83.7 g (0.2 mol) of 2,2-bis-(3-acetamidophenyl) hexafluoropropane are introduced in portions at 20°-30° C. into 400 ml of 95% by weight nitric acid. The reaction mixture is stirred for 30 minutes more and then poured onto 1,000 g of a mixture of water and ice. The precipitate is filtered off and washed with water until a pH of 3 is achieved. The dried crude product is suspended in 250 ml of ethanol and boiled for 5 minutes under reflux.

After cooling to 25° C., the solid is filtered off and dried at 100° C. Yield 89 g (0.18 mol); yellow solid; m.p. 187°–189° C.

Analysis values in %: $C_{19}H_{14}F_6N_4O_6$ calc.: C 44.89, H 2,87, F 22.43, N 11.02, O 18.89. (508.33) found: C 45.2, H 2.7, F 22.0, N 11.3, O 18.9.

$^1$H-NMR (CDCl$_3$)δ(ppm): 10.3 s 2 NH, 9.0 s 2 H, 8.25 d 2 H, 7.25 d 2 H, 2.3 s 2 CH$_3$.

$^{19}$F-NMR (CDCl$_3$)δ(ppm): −63.7 s CF$_3$.

(3) Preparation of
2,2-Bis-(3-amino-4-nitrophenyl)hexafluoropropane (9)

160 g (0.31 mol) of 2,2-bis-(3-acetamido-4nitrophenyl) hexafluoropropane are heated under reflux for 15 minutes in a solution of 65 ml of water, 570 ml of methanol and 25 g of sodium hydroxide. The hot solution is diluted with 1,300 ml of hot water and then cooled to 0°–5° C. The solid is filtered off with suction, washed with water, dried at 80° C. and recrystallized from toluene. Yield 115 g (0.27 mol); yellow solid; m.p. 257°–259° C.

Analysis values in %:
$C_{15}H_{10}F_6N_4O_4$ calc.: C 42.46, H 2,38, F 26.87, N 13.21, O 15.09.

(424.26) found: C 42.7, H 2.3, F 27.2, N 13.6, O 15.5.

$^1$H-NMR (d$^6$-DMSO)δ(ppm): 8.2 d 2 H, 7.8 s 2 NH$_2$, 7.4 s 2 H, 6.7 d 2 H.

$^{19}$F-NMR (d$^6$-DMSO)δ(ppm): −62.1 s CF$_3$.

(4) Preparation of
2,2-Bis-(3,4-diaminophenyl)hexafluoropropane (1)

96.7 g (0.23 mol) of 2,2-bis-(3-amino-4-nitrophenyl) hexafluoropropane are dissolved in 1,000 ml of ethyl acetate and reduced with hydrogen (100 bar) at 25° C. in an autoclave after the addition of 3 g of a palladium/charcoal catalyst (5% Pd). After filtering off the catalyst, the ethyl acetate is separated off on the rotary evaporator. The residue is taken up using 1 l of water and adjusted to a pH of 1 using 1:1 hydrochloric acid. The mixture is then heated to 70°–80° C., 20 g of activated charcoal are added, the mixture is stirred at 70°–80° C. for 15 minutes and the activated charcoal is filtered off. The colorless filtrate is saturated with nitrogen and is adjusted at 10°–20° C. to a pH of 7 using 1:1 ammonia solution under inert gas. The precipitate is separated off, washed well with water and dried to constant weight under reduced pressure. Yield 74 g (0.20 mol); gas chromatographic purity above 99.9%; white solid; m.p. 218°–220° C.

Analysis values in %:
$C_{15}H_{14}F_6N_4$ calc.: C 49.45, H 3.87, N 15.38, F 31.29. (364.29) found: C 49.4, H 3.7, N 15.8, F 30.9.

$^1$H-NMR (d$^6$-DMSO)δ(ppm): 6.4–6.5 m 6 H, 4.6 s 4 NH$_2$.

$^{19}$F-NMR (d$^6$-DMSO)δ(ppm): −62.44 s CF$_3$.

IR (KBr) γ: 3430 and 3350 cm$^{-1}$ (—NH$_2$), 1260–1130 cm$^{-1}$ (—CF$_3$).

We claim:
1. A compound of the formula

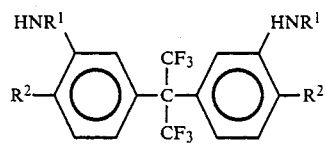

wherein R$^1$ is hydrogen or an acyl group in which a nonaromatic hydrocarbon group of 1 to 6 carbon atoms is attached to the CO-group and R$^2$ is H or NO$_2$ if R$^1$ is an acyl group, and is NO$_2$, if R$^1$ is hydrogen.

2. The compound as claimed in claim 1, wherein R$^1$ as an acyl group is an acetyl group and R$^2$ is hydrogen or NO$_2$.

3. The compound as claimed in claim 1, wherein R$^1$ is hydrogen and R$^2$ is NO$_2$.

4. A process for the production of 2,2-bis-(3,4-diaminophenyl)-hexafluoropropane of the formula

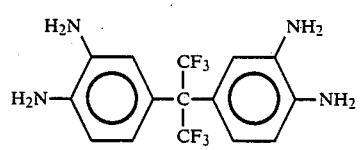

which comprises
(a) acylating 2,2-bis-(3-aminophenyl)-hexafluoropropane, under conditions conventional for acylations, to yield a 2,2-bis-(3-acylamidophenyl)-hexafluoropropane, the acyl group of which is free from aromatic groups,
(b) nitrating the 2,2-bis-(3-acylamidophenyl)-hexafluoropropane, under conditions conventional for nitrations, to yield 2,2-bis-(3-acylamido-4-nitrophenyl)-hexafluoropropane,
(c) deacylating the 2,2-bis-(3-acylamido-4-nitrophenyl)-hexafluoropropane, under conditions conventional for deacylations, to yield 2,2-bis-(3-amino-4-nitrophenyl)-hexafluoropropane,
(d) reducing this compound, under conditions conventional for the reduction of nitro compounds, to yield 2,2-bis-(3,4-diaminophenyl)-hexafluoropropane, and
(e) isolating 2,2-bis-(3,4,-diaminophenyl)-hexafluoropropane or subjecting it to a purification by converting it into a solution of one of its salts, adsorbing contaminations at an adsorption agent and precipitating the 2,2-bis-(3,4-diaminophenyl)hexafluoropropane by addition of a base.

5. The process as claimed in claim 4, wherein the acylation is carried out with an acid halide or an acid anhydride.

6. The process as claimed in claim 5, wherein in the acylating compound a hydrocarbon group of 1 to 6 carbon atoms is attached to the CO-group.

7. The process as claimed in claim 6, wherein the acylation is an acetylation.

8. The process as claimed in claim 7, wherein the acetylation is carried out with acetanhydride.

9. The process as claimed in claim 4, wherein the reduction in step (d) is carried out catalytically with hydrogen at a transition metal.

10. The process as claimed in claim 4, wherein at least one condition selected from the group consisting of
(a) the acylation is carried out at a temperature in the range of from 0° to 50° C., (b₁) the nitration is carried out with a nitric acid of 85 to 95 % strength by weight, (b₂) the acylated compound obtained in step (a) is introduced into the nitric acid-water-mixture, (c₁) the deacylation is carried out in a solution of the acylated compound in water or a solvent miscible with water, or a combination thereof, which solution contains from 5 to 50 % by weight of a base, (c₂) the deacylation is effected at a temperature in the range of from 0° to 100° C., (d) the reduction is carried out catalytically with hydrogen and a transition metal of group VIII of the Periodic System, (e₁) the 2,2-bis-(3,4-diaminophenyl)-hexafluoropropane is converted into a solution of one of its salts while excluding oxygen, (e₂) the said 2,2-bis-(3,4-diaminophenyl)-hexafluoropropane is converted into a hydrohalide, (e₃) the adsorption agent is activated charcoal, (e₄) the 2,2-bis-(3,4-diaminophenyl)-hexafluoropropane is precipitated by an aqueous solution of ammonia and (e₅) the precipitation of the 2,2-bis-(3,4-diaminophenyl)-hexafluoropropane by addition of the base is effected under exclusion of oxygen is applied therein.

11. The process as claimed in claim 10, wherein at least one condition selected from the group consisting of (a) the acylation is carried out at a temperature in the range of from 5° to 20° C., (b₂) the acylated compound is introduced into the nitric acid-water-mixture at a temperature in the range of from 0° to 40° C., (c₁) the deacylation is effected in a solution of an alcohol, and (e₂) the 2,2-bis-(3,4-diaminophenyl)-hexafluoropropane is converted into a solution of the hydrochloride is applied therein.

12. The process as claimed in claim 4, wherein the conversion of the 2,2-bis-(3,4-diaminophenyl)-hexafluoropropane into one of its salts and the precipitation of the 2,2-bis-(3,4-diaminophenyl)-hexafluoropropane with a base is carried out under exclusion of oxygen.

13. A process for the production of 2,2-bis-(3,4-diaminophenyl)-hexafluoropropane of the formula

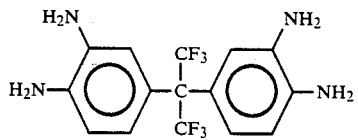

which comprises
(a) acylating 2,2-bis-(3-aminophenyl)-hexafluoropropane with an acid halide or an acid anhydride at a temperature in the range of from 0° to 50° C. to yield a 2,2-bis-(3-acyl- amidophenyl)-hexafluoropropane, the acyl group of which is free from aromatic groups, (b) nitrating the 2,2-bis-(3-acylamidophenyl)-hexafluoropropane with a nitric acid of 85 to 95% strength by weight to yield 2, 2-bis-(3-acylamido-4-nitrophenyl)-hexafluoropropane, (c) deacylating the 2,2-bis-(3-acylamido-4-nitrophenyl)-hexafluoropropane at a temperature in the range of from 0° to 100° C. in a solution of the acylated compound in water, a solvent miscible with water, or a combination thereof, which solution comprises from 5 to 50% by weight of a base, to yield 2,2-bis-(3-amino-4-nitrophenyl)-hexafluoropropane, (d) reducing 2,2-bis(3-amino-4-nitrophenyl)-hexfluoropropane catalytically with hydrogen and a transition metal of group vIII of the periodic system to yield 2,2-(bis-(3,4-diaminophenyl)-hexafluoropropane.

14. A process for the production of 2,2-bis-(3,4-diaminophenyl)-hexafluoropropane of the formula

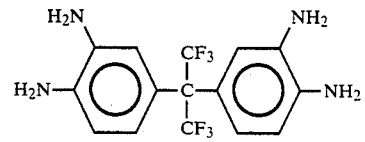

which comprises
(a) acylating 2,2-bis-(3-aminophenyl)-hexafluoropropane with an acid halide or an acid anhydride at a temperature in the range of from 0° to 50° C. to yield a 2,2-bis-(3-acyl- amidophenyl)-hexafluoropropane, the acyl group of which is free from aromatic groups, (b) nitrating the 2,2-bis-(3-acylamidophenyl)-hexafluoropropane with an effective amount of nitric acid of 85 to 95% strength by weight to yield 2,2-bis-(3-acylamido-4-nitrophenyl)hexafluoropropane, (c) deacylating the 2,2-bis-(3-acylamido-4-nitrophenyl)-hexafluoropropane at a temperature in the range of from 0° to 100° C. in a solution of the acylated compound in water, a solvent miscible with water, or a combination thereof, which solution comprises from 5 to 50% by weight of a base, to yield 2,2-bis-(3-amino-4-nitrophenyl)-hexafluoropropane, (d) reducing this compound catalytically with hydrogen and a transition metal of group VIII of the periodic system to yield 2,2-bis-(3,4-diaminophenyl)-hexafluoropropane, and (e) subjecting this compound to purification by converting it into a solution of one of its salts, adsorbing the contaminants on an adsorption agent and precipitating the 2,2-bis-(3,4-diaminophenyl)-hexafluoropropane by addition of a base.

15. The process as claimed in claim 14, wherein step (e) further comprises:

(e₁) converting the 2,2-bis-(3,4-diammophenyl)-hexafluoropropane in a solution of a hydrohalide, (e₂) absorbing the contaminants on activated charcoal, and (e₃) precipitating the 2,2-bis-(3,4-diaminophenyl)-hexafluoropropane with an aqueous solution of ammonia.

16. The process of claim 14, wherein, in said step (e), the conversion of the 2,2-bis-(3,4-diaminophenyl)-hexafluoropropane into one of its salts and the precipitation of the 2,2-bis-(3,4-diaminophenyl)-hexafluoropropane with a base is carried out under the exclusion of oxygen.

* * * * *

UNITED STATES PATENT AND TRADEMARK OFFICE
CERTIFICATE OF CORRECTION

PATENT NO. : 4,922,019
DATED : May 1, 1990
INVENTOR(S) : JURGEN LAU, ET AL.

It is certified that error appears in the above-identified patent and that said Letters Patent is hereby corrected as shown below:

ON TITLE PAGE:
In the Abstract, second to last line,

"recipitating" should read -- precipitating -- .

Column 1, lines 14-15, "tertamine" should read -- tetramine -- .

Column 4, lines 55-56, "O 8.90. 25 (418.34)" should read

-- O 8.90 (418.34) -- .

In Claim 13, column 8, lines 10-11,

"-hexfluoropropane" should read -- -hexafluoropropane -- .

In Claim 13, column 8, line 12, "vIII" should read -- VIII -- .

In claim 15, column 8, line 52, "diammophenyl" should read

-- diaminophenyl -- .

In Claim 15, column 8, line 54, "absorbing" should read --adsorbing--.

Signed and Sealed this

Twenty-second Day of October, 1991

Attest:

HARRY F. MANBECK, JR.

*Attesting Officer*    *Commissioner of Patents and Trademarks*